United States Patent [19]

Hansen et al.

[11] Patent Number: 4,662,914
[45] Date of Patent: May 5, 1987

[54] FLOW-LIMITED DIRECT GC/MS INTERFACE

[75] Inventors: Stuart C. Hansen, Palo Alto; Jean-Luc Truche, Los Altos, both of Calif.

[73] Assignee: Hewlett-Packard Company, Palo Alto, Calif.

[21] Appl. No.: 712,840

[22] Filed: Mar. 18, 1985

[51] Int. Cl.⁴ .......................................... B01D 15/08
[52] U.S. Cl. ..................................... 55/386; 55/197; 422/70
[58] Field of Search ............... 55/197, 386; 210/198.2; 422/70

[56] References Cited

U.S. PATENT DOCUMENTS

| 3,936,374 | 2/1976 | Bradley et al. ................... 55/197 X |
| 4,391,778 | 7/1983 | Andresen et al. ................ 422/70 X |
| 4,394,263 | 7/1983 | Dosch et al. ..................... 210/198.2 |
| 4,453,954 | 6/1984 | Kolb et al. ........................... 55/386 |

*Primary Examiner*—Robert Spitzer
*Attorney, Agent, or Firm*—John A. Frazzini

[57] ABSTRACT

A capillary-direct interface, suitable for connecting a gas chromatograph to a mass spectrometer, having a flow restrictor that is to be mounted at the entrance to the ionization chamber of the mass spectrometer to prevent damage to the mass spectrometer if the column of the gas chromatograph is removed from the mass spectrometer or breaks inside the interface. A preferred flow restrictor includes a hollow tube, the middle of which is connected to an exhaust port to enable a vacuum pump to remove gas from the middle of the tube. The hollow tube is enclosed by a high thermal conductivity tube that is thermally connected to a heat source to control the temperature of the hollow tube. A capillary GC column can be inserted entirely through the hollow tube into the ionization chamber to produce a capillary direct mode of coupling. Also, an additional capillary tube, inside the hollow tube and extending from the ionization and detection chamber to the end of the GC column, can be used to implement the open-split and jet separator modes of coupling.

7 Claims, 6 Drawing Figures

4,662,914

FLOW-LIMITED DIRECT GC/MS INTERFACE

BACKGROUND OF THE INVENTION

This invention relates in general to mass spectrometers and gas chromatographs (such as gas or liquid types, or direct solid or liquid types) and relates more particularly to an interface that provides a direct path to the ion source and also enables a column of a gas chromatograph to be easily decoupled from the mass spectrometer without cooling and venting or risk of damage to the spectrometer. Modern gas chromatograph/mass spectrometer (GC/MS) instruments utilize gas chromatograph (GC) columns to enhance standard chromatographic results. In such an instrument, a sample is introduced at a pressure on the order of 30 pounds per square inch (psi) into a GC column. The temperature of the GC column is controlled to ramp up to a maximum temperature T sufficiently high to vaporize the entire sample.

In one typical system, the GC column is flexible fused silica having an outside diameter on the order of 0.4 mm and an inside diameter on the order of 0.2–0.3 mm. A vaporized sample is injected into an entrance end of the GC column and the various components of the sample travel along the GC column and out through an exit end of the GC column. The inside of the column has a coating that interacts with the vaporized sample in such a way that the components of the sample travel at various velocities along the column. As a result of the velocity differences, there is a separation in time between the emission of the various components through the exit end of the GC column. The GC column therefore functions to separate the components of the sample. In a GC/MS, the exit end of the capillary column is inserted into the ionization and detection chamber of a mass spectrometer (MS) to identify the various components of the sample.

In the ionization and detection chamber, the vaporized sample components are fragmented (e.g., by bombardment with electrons). The fragments are ionized (e.g., by chemical ionization of electron ionization) and then passed through an electric and/or magnetic field (mass analyzer) that separates the fragments on the basis of their ratio of mass to ionized charge. Each component has a characteristic distribution of quantity of fragments as a function of fragment mass. This distribution serves as a fingerprint that enables identification of each sample component. In order to separate the fragments in the mass analyzer, the pressure in the mass spectrometer is kept low enough (on the order of $10^{-6}$–$10^{-5}$ Torr) that the mean free path length of the ionized fragments is much longer than the typical linear dimension of the mass spectrometer ionization and detection chamber.

There are three common types of interface between the gas chromatagraph and the mass spectrometer. In the first type, known as the capillary direct interface, the capillary column is inserted directly into the mass spectrometer's ionization chamber. This interface has the highest sensitivity because the sample components are injected directly into the ionization and detection chamber. However, it is very time consuming to change the GC column in such an interface. The ionization chamber has electrodes that are at about 250 degrees Centigrade and that will oxydize rapidly if near atmospheric pressure air is allowed into the chamber. Therefore, when the GC column is to be changed, the electrodes in the ionization chamber must be allowed to cool below 100 degrees Centigrade before air is allowed to controllably leak into the ionization chamber—a process that can take on the order of 45 minutes. The vacuum in the ionization chamber must then be reestablished before the mass spectrometer is again used.

The second type of interface, known as the open-split interface, is utilized when it is advantageous to have a larger flow rate in the GC column than is allowed to flow into the mass spectrometer. Typically, the flow rate into the mass spectrometer is limited to less than 1 milliliter/minute. This flow rate may be below the rate that optimizes the GC separation process. To allow this difference in flow rates, this interface utilizes a capillary tube that connects the MS ionization and detection chamber to one end of a cylindrical connection chamber. The exit end of the GC column is inserted into the other end of the connection chamber substantially collinear with the capillary tube. A small gap (on the order of 2.0 mm) is left between the exit end of the GC olumn and the end of the capillary tube to enable the excess flow in the GC column to spill out into the connection chamber. The connection chamber has an exhaust port near one end to allow the excess flow to leave the connection chamber. An inlet port is located near the other end of the connection chamber to allow a purge gas to be supplied to assist removal of the excess gas flow from the connection chamber. For 6 mm packed columns, this approach has the disadvantage of reduced sensitivity because only a portion (on the order of 3%) of the sample enters the MS detector. For capillary columns, this approach has the disadvantage of degradation of the chromatographic resolution because of internal dead volume in the connection chamber.

The third interface type, known as the jet separator interface, is utilized when it is desired to remove lightweight carrier gases from the sample gas before the sample gas enters the mass spectrometer. This action reduces the total gas load on the mass spectrometer vacuum pumps to a manageable flow (throughput Q). The structure of this interface is very similar to that in the open split interface, except that the exit end of the GC column is tapered to produce a jet of the gases emitted from the exit end of the GC column. In many applications, a light carrier gas is utilized in the GC column to carry the sample gas components along the GC column. The molecules of the light carrier gas have a high enough diffusion rate that they diffuse out of the jet, thereby increasing the concentration of sample gas components entering the capillary column. Unfortunately, this interface also has the disadvantage of losing some of the sample gas components in the gap between the GC column and the capillary tube.

In each of these methods, the mass spectrometer can be damaged by the inrush of air if the tubing entering the ionization chamber is broken. It would therefore be advantageous to have a new interface that combines the benefits of the above interfaces and that protects the mass spectrometer from damage.

SUMMARY OF THE INVENTION

The disclosed interface contains a flow restrictor attached at the entrance port to the ionization and detection chamber of the mass spectrometer. The flow restrictor provides sufficient resistance to flow of gases into the ionization and detection chamber that, if the GC column is broken inside the interface or removed from the mass spectrometer, the flow restrictor will limit flow of ambient gases into the chamber to a rate that will not result in damage to the mass spectrometer. A suitable flow restrictor is a tube having a combination of length and inside diameter sufficient to produce a flow conductance that is low enough to produce the desired limited flow of ambient gases into the ionization and detection chamber. Preferably, the inside diameter is slightly larger than the outside diameter of a typical capillary GC column so that such a capillary column can be passed entirely through the flow restrictor to produce a capillary direct type of interface.

In accordance with the illustrated preferred embodiment, the flow restrictor includes a first tube, a second tube, a first connection chamber and an optional second connection chamber. The first tube connects the entrance port of the MS ionization and detection chamber to one end of the first chamber and the second tube, collinear with the first tube, connects the other end of the first chamber to a first end of the second chamber. In the other end of the second chamber is an aperture through which a GC column can be inserted. The inside diameter of the first tube is slightly larger than the outside diameter of a typical GC capillary column and the inside diameter of the second tube is slightly larger than the outside diameter of the largest GC column that will typically be used. The first chamber has an exhaust port that is to be connected to a vacuum pump to reduce the pressure in the first chamber. The optional second chamber has an entrance port through which a purge gas can be supplied to displace air and/or to help sweep sample gases out of the first and second tubes. The inclusion of the first chamber held at below atmospheric pressure enables the total length of the interface to be significantly less than if a single tube were utilized as the flow restrictor. A temperature regulator is also included to control the temperature of the first and second tubes.

This interface can be operated in the capillary direct mode, in the open-split mode or in the jet separator mode. The diameters and lengths of the first and second tubes and the vacuum in the first chamber are selected to avoid damage to the mass spectrometer even if the GC column is broken internally or removed from the interface. The GC column can therefore be easily and quickly changed.

DESCRIPTION OF THE PREFERRED EMBODIMENT

Figure 1:
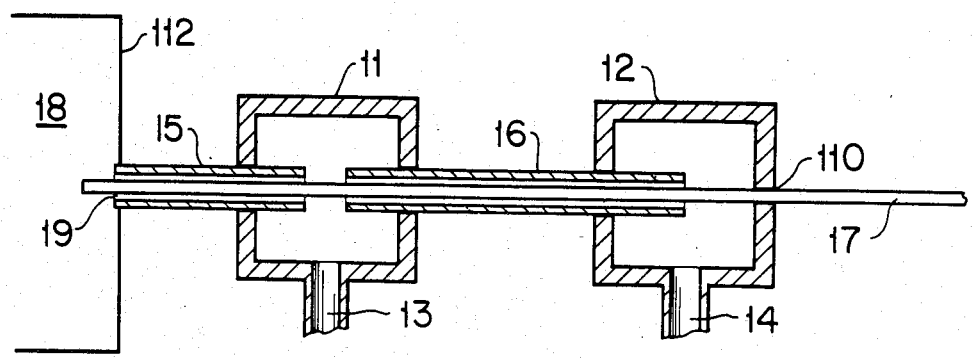
FIG. 1 illustrates schematically the interface in the capillary direct mode.

FIG. 1 shows schematically the interface being operated in the capillary direct mode of operation. The interface includes a first chamber 11, a second chamber 12, a first tube 15 and a second tube 16. Tube 15 is attached to a mass spectrometer 112 at the entrance port 19 of the ionization chamber 18 of the mass spectrometer (MS). Tubes 15 and 16 are collinear with one another and with an entrance aperture 110 in chamber 12 so that a GC capillary column 17 can be inserted through the interface into the MS ionization and detection chamber.

Figure 2:
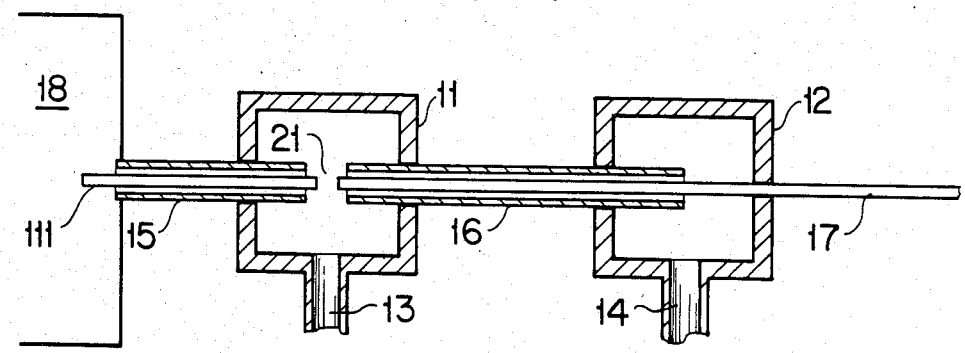
FIG. 2 illustrates schematically the interface in the jet separator mode.
Figure 3:
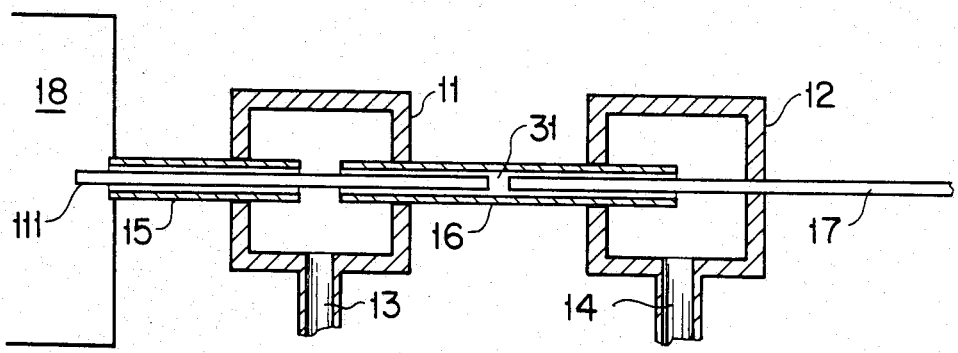
FIG. 3 illustrates schematically the interface in the open-split mode.

The inside diameter of tube 15 is selected to be slightly larger than the outside diameter of the largest GC capillary column to be used in the GC/MS system. The amount by which the inside diameter of tubes 15 and 16 should be larger than the outside diameter of the capillary GC column should be the minimum amount that allows the capillary GC column to be easily fed through tubes 15 and 16. With this choice of diameters, a GC capillary column 17 can be inserted entirely through the interface to produce a capillary direct mode as in FIG. 1. In both the jet separator mode (FIG. 2) and the open-split mode (FIG. 3), a capillary tube 111 is used in conjunction with GC column 17. In both of these modes, capillary tube 111 that functions as a flow restrictor is collinear with GC column 17 and there is a small gap (on the order of 0.2 mm) between the closest ends of tube 111 and column 17. However, in the jet separator mode, gap 21 is located in the space between tubes 15 and 16, whereas, in the open-split mode, gap 31 is located inside of tube 16.

Chamber 11 contains an exhaust port 13 that is to be coupled to a vacuum pump (not shown) to reduce the pressure in chamber 11 below atmospheric pressure. The utilization of the vacuum pump enables the length of the interface to be significantly shorter than it would have to be without the vacuum pump. The selection of the vacuum pump pumping rate and the diameters and lengths of tubes 15 and 16 are selected to guarantee a maximum pressure in chamber 18 that prevents damage to the mass spectrometer (i.e., a maximum pressure $p_m$ on the order of $10^{-3}$ Torr) even if the GC column is broken or removed. These parameters are selected as follows.

If the GC column is removed from the GC/MS interface, then tubes 15 and 16 and the vacuum pump must in combination produce an effective conductance that limits air flow into chamber 18 to a level that can be handled by the mass spectrometer pump without letting the pressure in chamber 18 increase above $p_m$. The effect of the vacuum pumps on chamber 18 and attached to port 13 can be seen by reference to FIG. 6 in which the flow of gas through the interface is illustrated. In that figure, the pressures $P_1$, $P_2$, and $P_3$ represent atmospheric pressure, the pressure in chamber 11 and the pressure in chamber 18, respectively.

A pump is rated by its pumping speed S which is equal to the volume of gas pumped per unit time. The pumping speed of the pumps in chamber 18 and attached to port 13 are represented by $S_3$ and $S_2$, respectively. Because gases are compressible, the number N of molecules pumped per unit time varies directly with the pressure. This relationship is:

$$N = S*n = SP/kT$$

where n is the number of molecules per unit volume which, by the state equation for an ideal gas, is equal to P/kT where P is the pressure of the gas, k is Boltzmann's constant and T is the temperature. For isothermal flow, since T is a constant, this flow rate is conveniently represented by the throughput Q which is defined as being equal to SP.

Figure 6:
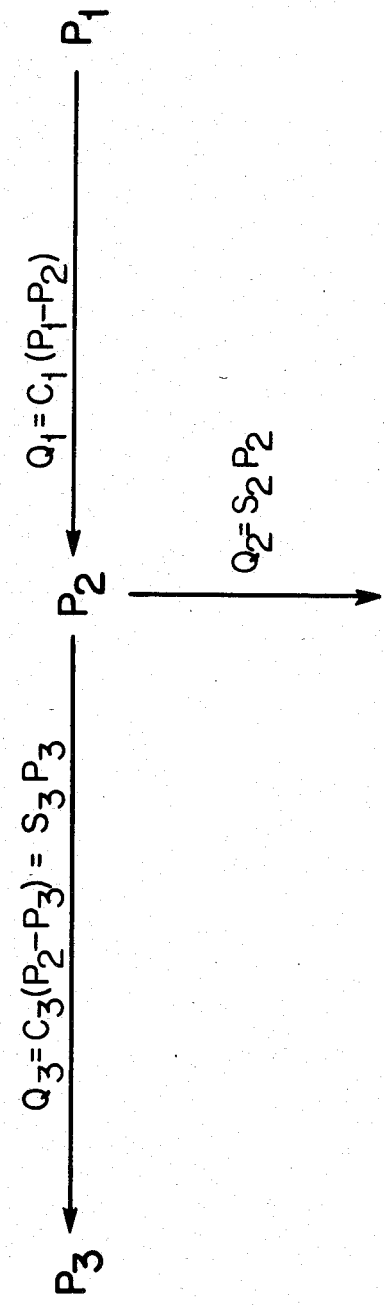
FIG. 6 shows the throughput Q in the interface.

Because of viscosity, the throughput Q of gas through a pipe is proportional to the pressure drop between the ends of the pipe. This proportionality factor is called the conductance. In FIG. 6, the conductance of pipes 16 and 15 are represented by $C_1$ and $C_2$, respectively. As is discussed in chapter 3 of the text entitled Vacuum Technology, written by A. Roth and published by North Holland publishers, the relationship between pipe diameter D, length L and conductance C is determined by the type of flow through the pipe. For air at 20 degrees Centigrade, diameter and length measured in centimeters, and pressure measured in Torrs, this relationship is:

$$C = 182 D^4 \bar{P}/L \quad \text{(viscous nonturbulent flow)}$$

$$C = 12.1 D^3/L \quad \text{(molecular flow)}$$

where $\bar{P}$ is the average of the pressures on each end of the pipe. The relationships between the pump speeds, conductances, and pressures is represented in FIG. 6. The pump attached to port 13 removes a quantity $Q_2$ of gas so that the quantiy $Q_3$ of gas flowing into chamber 18 is equal to $Q_1-Q_2$. Pipes 15 and 16 and the pump attached to port 13 combine to produce an effective conductance $C_e$ defined as $Q_3/P_1-P_3$). Since $P_3$ is maintained at less than $p_m$ which is much less than $P_1$, $C_e$ is substantially equal to $Q_3/P_1$. Likewise $C_3$ is substantially equal to $Q_3/P_2$. Thus, the ratio of $C_e$ to $C_3$ is $P_2/P_1$ or, equivalently, $C_e=(P_2/P_1)C_3$ which shows that $C_e$ can be made to be only several percent of $C_3$ due to pipes 15 and 16 and the pump on port 13.

$S_3$ and $P_m$ are determined by the mass spectrometer and are not free parameters in the design of the GC/MS interface. The pump speed $S_3$ and the conductances $C_1$ and $C_3$ are selected so that $P_3<P_m$ (or, equivalently, so that $Q_3<Q_m$ where $Q_m=S_2P_m$). Since the theoretical equations for gas flow are only approximations to the actual highly complex flow, these equations should be used for an initial selection of parameters and then the optimum parameters should be determined empirically.

These relationships between the parameters still leave one degree of freedom in the choice of lengths. This degree of freedom is removed by requiring that the total length of the interface be minized. In a particular embodiment (shown in FIGS. 4 and 5) tubes 15 and 16 are combined into a single tube 40 having an inside diameter of 0.78 mm and an overall length of 443 mm. The portion of tube 40 corresponding to tube 15 has a length of 236 mm.

Figure 4:
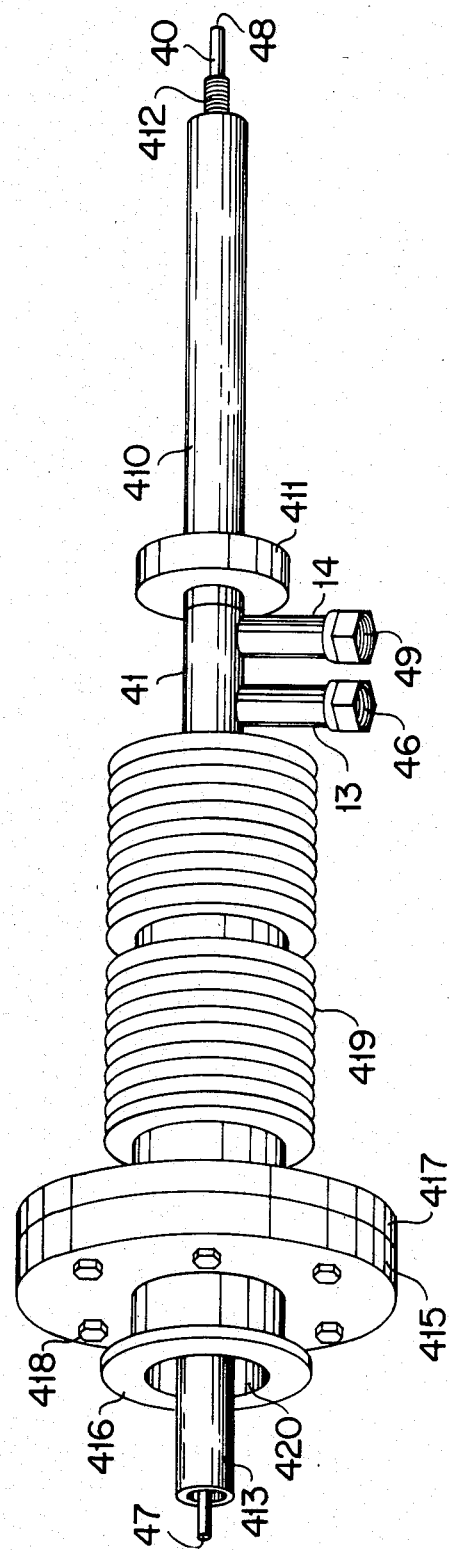
FIG. 4 shows the preferred embodiment of the interface.
Figure 5:
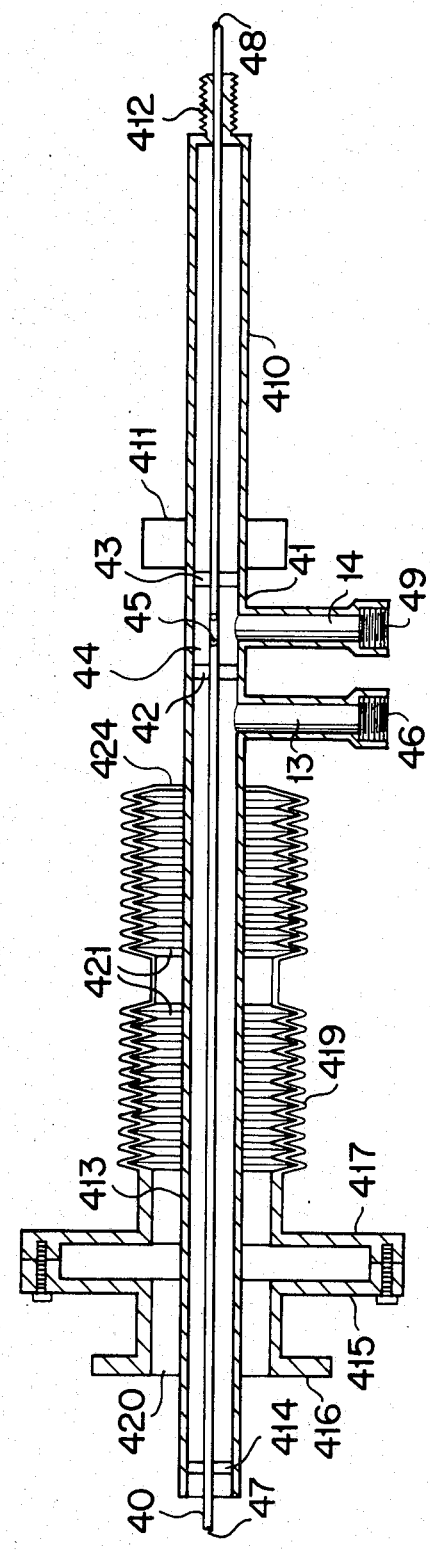
FIG. 5 is a cross-sectional view of the interface shown in FIG. 4.

FIGS. 4 and 5 present the preferred embodiment of the interface. In this embodiment, chamber 12 is not used and chamber 11 is defined by tube 41 and walls 42 and 43. A hollow tube 40 extends through an aperture in each of walls 42 and 43. A cavity 44 is located between tube 40 and 41 in the region between walls 42 and 43. An exhaust port 14 is connected by a fitting 49 to a vacuum pump (not shown) to reduce the pressure in cavity 44. End 47 of tube 40 is inserted into the ionization chamber of the mass spectrometer. The GC column is inserted into the interface through end 48 of tube 40. A set of holes 45 in tube 40 connect the inside of tube 40 to cavity 44. The portion of tube 40 between end 47 and the centroid of holes 45 is equivalent to tube 15 in FIGS. 1-3 and the portion of the 40 between end 48 and the centroid of holes 45 is equivalent to tube 16. An inlet 13 is connected by a fitting 46 to an accessory vacuum gauge sensor to detect the pressure in the annular passage between tubes 40 and 413.

It is advantageous to hold the temperature of tube 40 at substantially the maximum temperature T of the GC column. To achieve this, the portion of tube 40 between wall 43 and end 48 is enclosed by a tube 410 of high thermal conductivity material (e.g., a copper tube). A heat source 411 is attached to tube 410 to maintain its temperature substantially at T. A set of threads 412 on the end of tube 410 enables the interface to be attached to a nut and ferrule to secure the GC column. Tube 41 is of a higher thermal conductivity material so that it is at substantially the same temperature as tube 410. Likewise, the portion of tube 40 between wall 42 and end 47 is enclosed by a high thermal conductivity tube 413 which is in thermal contact with heat source 411 via tubes 41 and 410. Wall 42 and a multihole bushing 414 support tube 40 substantially in the center of tube 413.

In order to mount the interface to the mass spectrometer, a flange 416 of a coupling 415 is welded onto the mass spectrometer. Coupling 415 is secured to a coupling 417 by a set of bolts 418. Coupling 417 includes a metal bellows 419 which is terminated by wall 424. Cavity 421 within bellows 419 is connected through opening 420 to the ionization and detection chamber of the mass spectrometer, so that, when the ionization and detection chamber is evacuated, a vacuum is produced in cavity 421. This helps to reduce heat loss from tube 40, thereby maintaining the temperature of tube 40 at substantially the maximum GC temperature T.

We claim:

1. An interface that is suitable for connecting a chromatograph to a mass spectrometer having an ionization and detection chamber which can be damaged during operation of the mass spectrometer by a leakage of air into the ionization and detection chamber at greater than a throughput $Q_m$, said mass spectrometer to be operated in an ambient external atmosphere at less than a maximum pressure P, said interface comprising:
    a flow restrictor having an effective flow conductance $C_e$ less than $Q_m/P$;
    means for attaching the flow restrictor to the mass spectrometer at an entrance port to the ionization and detection chamber; and
    means for coupling a GC column to the flow restrictor so that gases flowing through the GC column flow through the flow restrictor into the ionization and detection chamber of the mass spectrometer;
    said flow restrictor including a means for inserting said GC column through the flow restrictor directly into the ionization and detection chamber, whereby exchange of capillary columns in a capillary direct mode of operation can be effectuated without needing the time consuming steps of cooling, venting, pumping down and reheating the mass spectrometer during such exchange.

2. An interface as in claim 1 wherein the flow conductance $C_e$ is substantially equal to $Q_m/P$.

3. An interface as in claim 1 wherein the flow restrictor comprises a hollow tube having a combination of length and diameter such that its flow conductance $C_e$ is substantially equal to $Q_m/P$.

4. An interface as in claim 3 wherein the hollow tube has an internal diameter slightly larger than the outside diameter of the largest diameter GC column that will be utilized in the gas chromatograph.

5. An interface as in claim 1 wherein the flow restrictor comprises:
    a hollow tube that, at an intermediate point R along its length, has at least one lateral opening;

an exhaust port connected to said at least one opening; and a pump, connected to the exhaust port, that reduces the pressure at point R to a level that produces for the interface an effective flow conductance $C_e$ less than $Q_m/P$.

6. An interface as in claim 5 wherein the region of the hollow tube containing said at least one lateral opening is enclosed by a chamber to which the exhaust port is connected.

7. An interface as in claim 6 further comprising an entrance port connected to said chamber, whereby a purge gas supply can be connected to this entrance port to supply a purge gas to assist in purging gases in said chamber.

* * * * *